(12) United States Patent
Qian et al.

(10) Patent No.: US 9,139,430 B2
(45) Date of Patent: Sep. 22, 2015

(54) COMPOSITE NANOGRANULES FROM POLYMER/INORGANIC NANOPARTICLES, PREPARATION METHOD THEREOF AND USE OF THE SAME

(75) Inventors: Suping Qian, Jiangsu (CN); Yuhong Xu, Jiangsu (CN); Zhentian Fan, Jiangsu (CN); Yongtai Hou, Jiangsu (CN)

(73) Assignee: Wuxi Now Materials Corp., Wuxi, Jiangsu (CN)

( * ) Notice: Subject to any disclaimer, the term of this patent is extended or adjusted under 35 U.S.C. 154(b) by 25 days.

(21) Appl. No.: 13/320,371

(22) PCT Filed: May 12, 2010

(86) PCT No.: PCT/CN2010/072657
§ 371 (c)(1),
(2), (4) Date: Nov. 14, 2011

(87) PCT Pub. No.: WO2010/130206
PCT Pub. Date: Nov. 18, 2010

(65) Prior Publication Data
US 2012/0064140 A1 Mar. 15, 2012

(30) Foreign Application Priority Data
May 12, 2009 (CN) .......................... 2009 1 0135275

(51) Int. Cl.
| | |
|---|---|
| A01N 25/26 | (2006.01) |
| A01N 37/22 | (2006.01) |
| A01N 43/56 | (2006.01) |
| A01N 53/14 | (2006.01) |
| B82Y 30/00 | (2011.01) |
| B82Y 5/00 | (2011.01) |
| C08K 9/10 | (2006.01) |
| A61K 31/337 | (2006.01) |
| A01N 57/16 | (2006.01) |
| C08L 25/14 | (2006.01) |
| C08F 20/18 | (2006.01) |
| C08J 3/12 | (2006.01) |
| C08J 3/20 | (2006.01) |
| C09C 1/22 | (2006.01) |
| C09C 1/30 | (2006.01) |
| C09C 3/10 | (2006.01) |
| C09D 5/02 | (2006.01) |
| C09D 7/12 | (2006.01) |
| A61K 9/10 | (2006.01) |

(52) U.S. Cl.
CPC ................. *B82Y 30/00* (2013.01); *C08F 20/18* (2013.01); *C08J 3/12* (2013.01); *C08J 3/128* (2013.01); *C08J 3/20* (2013.01); *C09C 1/22* (2013.01); *C09C 1/309* (2013.01); *C09C 1/3045* (2013.01); *C09C 1/3072* (2013.01); *C09C 3/10* (2013.01); *C09D 5/02* (2013.01); *C09D 7/1225* (2013.01); *A61K 9/10* (2013.01); *C01P 2002/52* (2013.01); *C01P 2002/54* (2013.01); *C01P 2004/04* (2013.01); *C01P 2004/61* (2013.01); *C01P 2004/62* (2013.01); *C01P 2004/64* (2013.01); *C08J 2383/02* (2013.01); *C08K 9/10* (2013.01)

(58) Field of Classification Search
CPC ... A61K 9/10; C01P 2002/52; C01P 2004/61; C01P 2004/62; C01P 2004/64; C09C 1/3045
See application file for complete search history.

(56) References Cited

U.S. PATENT DOCUMENTS

| | | | | |
|---|---|---|---|---|
| 4,940,729 | A | * 7/1990 | Matthewson | ............... 514/521 |
| 6,833,192 | B1 | * 12/2004 | Caruso et al. | ............... 428/403 |
| 7,273,842 | B1 | 9/2007 | VanDyk et al. | |
| 2003/0055178 | A1 | 3/2003 | Gore et al. | |
| 2003/0146529 | A1 | 8/2003 | Chen et al. | |
| 2004/0029978 | A1 | 2/2004 | Chane-Ching | |
| 2005/0065238 | A1 | 3/2005 | Lark | |
| 2005/0271745 | A1 | * 12/2005 | Gruettner et al. | ............ 424/646 |
| 2007/0281324 | A1 | 12/2007 | Perriat et al. | |
| 2008/0014357 | A1 | 1/2008 | Cayton et al. | |
| 2008/0187595 | A1 | 8/2008 | Jordan et al. | |
| 2009/0053512 | A1 | 2/2009 | Pyun et al. | |
| 2009/0115095 | A1 | 5/2009 | Kwak | |
| 2009/0297615 | A1 | * 12/2009 | Wang et al. | ................ 424/490 |

FOREIGN PATENT DOCUMENTS

| | | |
|---|---|---|
| CN | 1369511 A | 9/2002 |
| CN | 1530327 A | 9/2004 |
| CN | 1530397 A | 9/2004 |
| CN | 1583575 A | 2/2005 |
| CN | 679579 A | 10/2005 |
| CN | 101016403 A | 8/2007 |
| CN | 101245126 A | 8/2008 |
| JP | 09-194208 | 7/1997 |

(Continued)

OTHER PUBLICATIONS

Hrkach et al., Macrmolecules, 1995, 28, 4736-4739.*

(Continued)

*Primary Examiner* — Kyle Purdy
(74) *Attorney, Agent, or Firm* — RatnerPrestia (57) ABSTRACT

Composite nanogranules from polymer/inorganic nanoparticle, especially first composite nanogranules which are formed from first polymer and inorganic nanoparticles, second composite nanogranules which are obtained by forming second polymer on the first composite nanogranules, third composite nanogranules which is obtained by forming third polymer on the second composite nanogranules, and $N^{th}$ composite nanogranules which is obtained by forming $N^{th}$ polymer on the $(N-1)^{th}$ composite nanogranules with the similar method, are disclosed. A composition comprising anyone of the composite nanogranules described above is disclosed. The preparation method thereof and use of the same are also disclosed.

8 Claims, 3 Drawing Sheets

(56) References Cited

FOREIGN PATENT DOCUMENTS

| JP | 2009-79106 | 4/2009 |
|---|---|---|
| WO | WO 00/44507 | 8/2000 |
| WO | WO 2006/008120 A1 | 1/2006 |
| WO | WO 2006/106513 A2 | 10/2006 |
| WO | WO 2007/145285 A1 | 12/2007 |
| WO | WO 2008/028641 A2 | 3/2008 |
| WO | WO 2008/034675 A1 | 3/2008 |
| WO | WO 2008/051616 A2 | 5/2008 |

OTHER PUBLICATIONS

International Search Report dated Aug. 5, 2010.
Franca Tiarks et al., "Silica Nanoparticles as surfactants and fillers for latexes made by miniemulsion polymerization", *Langmuir*, 2001 (17): 5775-5789.
Dong-Ming Qi et al. "Anchoring of polyacrylate onto silica and formation of polyacrylate/silica nanocomposite particles via in situ emulsion polymerization", *Colloid Polym. Sci.*, 2008 (286): 233-241.
Hsieh et al., "Synthesis and electromagnetic properties of polyaniline-coated silica/maghemite nanoparticles," European Polymer Journal 45 (2009) 613-620.
Zhang et al., "Preparation and characterization of thermosensitive PNIPAA-coated iron oxide nanoparticles," Nanotechnology 19 (2008) 325608 (4pp).
Supplementary European Search Report for Application No. EP 10 77 4547 mailed Nov. 8, 2012.
International Application Serial No. PCT/CN2010/072657, International Search Report mailed Aug. 26, 2010, 4 pgs.
Li, Xiaoming, "Preparation and Characterization of $TiO_2$/PBA/PMMA Core-shell Particles", Journal of Dalian Institute of Light Industry, vol. 25 No. 4. (Dec. 2006), 257-261.
Xu, Peng, "The Study on Preparation and Properties of Polymers and Composite Nanoparticles", Chinese Doctoral Dissertation Full-text Database, Science and Technology, (Aug. 15, 2007).

\* cited by examiner

COMPOSITE NANOGRANULES FROM POLYMER/INORGANIC NANOPARTICLES, PREPARATION METHOD THEREOF AND USE OF THE SAME

CROSS-REFERENCE TO RELATED APPLICATIONS

This application is a U.S. National Phase Application of PCT International Application PCT/CN2010/072657, filed 12 May 2010 and published 18 Nov. 2010 in Chinese as WO 2010/130206A1, which claims priority from Chinese Application 200910135275.5, filed 12 May 2009, each of which is incorporated herein by reference in its entirety for all purposes.

FIELD OF THE INVENTION

The present invention relates to composite nanogranules from polymer/inorganic nanoparticle, especially first composite nanogranules which are formed from a first polymer and inorganic nanoparticles, second composite nanogranules which are obtained by forming second polymer at the first composite nanogranules, third composite nanogranules which are obtained by forming third polymer at the second composite nanogranules, and $N^{th}$ composite nanogranules which are obtained by forming $N^{th}$ polymer at the $(N-1)^{th}$ composite nanogranules in a similar way. The present invention further relates to a composition comprising anyone of the composite nanogranules described above. The present invention still relates to a coating material comprising anyone of the composite nanogranules described above. The present invention also relates to the preparation, modification and use of various nanogranules described above.

BACKGROUND OF THE INVENTION

Composite nanogranules from polymer/inorganic nanoparticle are one of the hot studies in the field of nano-technology due to the excellent mechanical, thermal, optical, electrical, and magnetic properties thereof, and is promised for wide application in various fields such as the fields of plastic, rubber, coating material, electronics, catalyst, medication, agricultural chemicals, and the like.

Chinese patent application publication CN1530397A discloses an mixed lactic acid polymer, which comprises multiple hydroxyl groups and multiple carboxyl groups, and can be used for nano-encapsulating pharmaceutical compounds, encapsulating or solubilizing Chinese herb extracts, solubilizing and dispersing the active ingredients of foods and comics, and solubilizing the ingredients of agricultural chemicals to prepare aqua-formulation of the agricultural chemicals. It also discloses that the polymer can be used for preparing inorganic nanoparticles such as $TiO_2$, ZnO, $Fe_3O_4$, $Fe_2O_3$, $CaCO_3$ and the like.

Chinese patent application publication CN1530327A discloses a method for preparing composite nanogranules of titanium oxide, which is produced by $TiCl_4$ alkali neutralization method from a polymeric chelating agent obtained by polymerizing a carboxylic acid and an alcohol. The nanogranules contain modification groups such as hydroxyl, carboxyl and hydrocarbyl, and are well dispersed in water.

Chinese patent application publication CN1583575A discloses a method for preparing superparamagnetic composite nanogranules, in which the superparamagnetic composite nanogranules are produced by mixing a polymeric chelating agent obtained by polymerizing a carboxylic acid and an alcohol with iron ions, and adding alkali. The obtained nanogranules have modification groups such as hydroxyl, carboxyl and alkyl, and thus can be further modified to obtain functionalized superparamagnetic nanogranules, which can be use in supporting drugs.

Franca Tiarks etc. (Silica Nanoparticles as surfactants and fillers for latexes made by microemulsion polymerization, *Langmuir,* 2001 (17): 5775-5789) reports a polymer dispersion prepared from various monomers by microemulsion polymerization, where the dispersions having different forms are produced by coupling co-monomers, silica nanogranules and hydrophobic components. In one case, the silica nanogranules are attached onto the particles of polymer latex, forming a dispersion having so called "hedgehog" form; while, in the other case, the silica nanogranules are completely wrapped into the polymer particle to form a dispersion having so called "raspberry" form. The obtained dispersions have a wide range of applications, for example, an anti-scratching agent in aqueous coatings.

QI Dong-ming et al. (Anchoring of polyacrylate onto silica and formation of polyacrylate/silica nanocomposite particles via in situ emulsion polymerization, *Colloid Polym. Sci.,* 2008 (286): 233-241) discloses polyacrylate/silica composite latex nanogranules, which are formed by in place emulsion polymerization of acrylate monomer adsorbed on silica nanogranules, where the polyacrylate is connected to the silica nanogranules by physical adsorption and chemical grafting, forming polyacrylate/silica composite latex nanogranules having "raspberry" form.

Although a lot of studies have been made, more composite nanogranules of polymer/inorganic nanoparticles having different structures and properties are still needed for satisfying various demands.

SUMMARY OF THE INVENTION

In a first aspect, the present invention provides composite nanogranules from polymer/inorganic nanoparticle, comprising at lease one inorganic nanoparticle and a first polymer, wherein the first polymer is presented in nanogranule form, and the at lease one inorganic nanoparticle is encapsulated in the first polymer, and wherein the at lease one inorganic nanoparticle is an inorganic nanoparticle containing doping elements, for example, silicon oxide, titanium oxide, alumina oxide, zinc oxide, iron oxide, cadmium selenide and zirconium oxide, wherein the doping elements are selected from iron, aluminum, silicon, lithium, sodium, potassium, beryllium, magnesium, calcium, strontium, barium, boron, gallium, indium, germanium, selenium, lead, nitrogen, phosphorus, arsenic, cobalt, nickel, copper, zinc, vanadium, titanium, manganese, and any combinations thereof.

In one embodiment, the composite nanogranules from polymer/inorganic nanoparticle have an average particles size of 1-1000 nm, for example 1-10 nm, 10-50 nm, 50-100 nm, 100-200 nm, 200-500 nm, 500-1000 nm, and the like.

In one embodiment, the first polymer contains hydrophilic groups, for example, carboxyl group, hydroxyl group, sulfonic group, amino group, or the combination thereof.

In one embodiment, the first polymer is at least partially branched or crosslinked polylactic acid, or a copolymer of lactic acid with $C_{2-27}$ fatty acids, $C_{2-27}$ fatty alcohols, saccharides, and/or amino acids.

In one embodiment, the saccharides comprise sucrose, lactose, trehalose, chitosan, mannose, glucose, galactose, maltose; the amino acids comprise glycine, lysine, leucine, arginine, cystine, cysteine, histidine, tryptophan, isoleucine, alanine, phenylalanine, serine, threonine, methionine, valine, tyrosine, aspartic acid, and any combinations thereof.

In one embodiment, the first polymer comprises 1-50 wt % linear polymer, 5-60 wt % branched polymer, and 5-60 wt % crosslinked polymer.

In a second aspect, the present invention provides composite nanogranules from polymer/inorganic nanoparticle, comprising at least one inorganic nanoparticle, a first polymer, a second polymer, and optionally an third polymer to a $N^{th}$ polymer, wherein N is an integer between 3 and 20, wherein the at least one inorganic nanoparticle is encapsulated in and/or attached onto the first polymer to form primary composite nanogranules, the second polymer is positioned in and/or attached onto the primary composite nanogranules to form secondary composite nanogranules, the third polymer is positioned in and/or attached onto the secondary composite nanogranules to form tertiary composite nanogranules, and similarly, the $N^{th}$ polymer is positioned in and/or attached onto the $(N-1)^{th}$ composite nanogranules to form $N^{th}$ composite nanogranules.

In one embodiment, the composite nanogranules from polymer/inorganic nanoparticle have an average particle size of 1-1000 nm, for example, 1-10 nm, 10-50 nm, 50-100 nm, 100-200 nm, 200-500 nm, 500-1000 nm, 1000-5000 nm, 5000-10000 nm, and the like.

In one embodiment, the first polymer contains hydrophilic groups such as carboxyl group, hydroxyl group, sulfonic group, amino group or the combinations thereof.

In one embodiment, the first polymer is at least partially branched or crosslinked polylactic acid, or a copolymer of lactic acid with $C_{2-27}$ fatty acids, $C_{2-27}$ fatty alcohols, saccharides, and/or amino acids.

In one embodiment, the saccharides comprise sucrose, lactose, trehalose, chitosan, mannose, glucose, galactose, maltose; the amino acids comprise glycine, lysine, leucine, arginine, cystine, cysteine, histidine, tryptophan, isoleucine, alanine, phenylalanine, serine, threonine, methionine, valine, tyrosine, aspartic acid, and any combinations thereof.

In one embodiment, the first polymer comprises 1-50 wt % linear polymer, 5-60 wt % branched polymer, and 5-60 wt % crosslinked polymer.

In one embodiment, the inorganic nanoparticles can be any of the inorganic nanoparticles that can be prepared in aqueous medium or that can be dispersed in aqueous medium, for example, silicon oxide, titanium oxide, aluminum oxide, zinc oxide, iron oxide, cadmium selenide, zirconium oxide, and any combinations thereof.

In one embodiment, the inorganic nanoparticles further contains doping elements, which are selected from iron, aluminum, silicon, lithium, sodium, potassium, beryllium, magnesium, calcium, strontium, barium, boron, gallium, indium, germanium, selenium, lead, nitrogen, phosphorus, arsenic, cobalt, nickel, copper, zinc, vanadium, titanium, manganese, and combinations thereof, and preferably from iron, aluminum, titanium, and any combinations thereof In one embodiment, the second polymer can be any of the polymers that can be formed in or on the primary composite nanogranules.

In one embodiment, the first polymer and the second polymer form a graft copolymer, a crosslinked copolymer, a sea-islands structure, an interpenetrating polymer network, or a semi-interpenetrating polymer network.

In one embodiment, the third polymer is the same as or different from the second polymer. The third polymer can be any of the polymers formed in or on the secondary composite nanogranule.

In one embodiment, the $N^{th}$ polymer is the same as or different from the $(N-1)^{th}$ polymer. The $N^{th}$ polymer can be any of the polymers formed in or on the $(N-1)^{th}$ composite nanogranule. The first polymer, the second polymer and the third polymer to optionally the $N^{th}$ polymer form a graft copolymer, a crosslinked copolymer, a sea-islands structure, an interpenetrating polymer network, or a semi-interpenetrating polymer network.

In one embodiment, the weight ratio of the first polymer to the inorganic nanoparticles is 100:1 to 1:100, and the weight ratios of the second to the Nth polymer to the inorganic nanoparticles are 1000:1 to 1:1000, respectively. For example, the weight ratio of the first polymer to the inorganic nanoparticles is 100:1 to 50:1, 50:1 to 1:1, 1:1 to 1:50, 1:50 to 1:100, and 0.5-5:100, 1.5:100, and the like; the weight ratio of the second polymer to the inorganic nanoparticles is 1000:1 to 1:1000, for example, 500:1 to 300:1, 300:1 to 50:1, 50:1 to 1:1, 1:50 to 1:300, 1:300 to 1:500, 1:500 to 1:1000, and 50-300:1, 100:1 and the like.

The examples of polymers can be used as the second to the $N^{th}$ polymers comprise homopolymers or copolymers formed from vinyl monomers. The vinyl monomers can be selected from α-olefin, vinyl chloride, acrylonitrile, vinylidene fluoride, tetrafluoroethylene, chlorotrifluoroethylene, $C_{1-20}$ alkyl esters of (meth)acrylic acid (e.g., methyl (meth)acrylate, ethyl acrylate, butyl acrylate, octyl acrylate, octadecyl acrylate, and the like), ethylene, propylene, isobutylene, butadiene, isoprene, isocyanate compounds, styrene, vinyl benzoate, isooctyl ester, 2-chloro-2-fluorinated ethylene, methyl cinnamate, maleates, 2,4-dichloro styrene, dimethyl propylene ether, methacrylic acid, maleic anhydride, vinyl alkyl ether, vinylidene chloride, methyl chlorinated acrylate, 4-N, N-dimethylamino-2-chloro styrene, 4-chloro styrene, methyl ethylene glycol, methacrylamide dimethylamine, vinyl stearate, 2-methyl pentyl ethylene, methyl acrylamide m-toluidine, trifluoro-methyl ethylene, isopropenyl methyl ketone, 3-fluoro-4-trifluoro methyl ethylene, dimethyl propenyl amine, divinyl sulfide, benzylidene-thienyl ethyl ketone, isopropyl methyl ketone, vinyl acetate, dicyclopentadiene, benzylidene-phenethyl ketone, furfuryl acetone, vinyl octoate, hydroxyethyl methacrylate, and combinations thereof.

In one embodiment, the composite nanogranules from polymer/inorganic nanoparticle further comprise low-molecular-weight organic compounds, which can be ones used in medicines, cosmics, foods, agricultural chemicals, catalysts, coatings, plastics, rubbers and composite materials, for example, active substances, solvents, aids, additives, or the like.

In a third aspect, the present invention provides a method for preparing the composite nanogranules from polymer/inorganic nanoparticle, comprising:

1) providing a first polymer; and
2) forming inorganic nanoparticles in or on the first polymer or encapsulating, depositing and/or adsorbing the formed inorganic nanoparticles at the first polymer.

In a forth aspect, the present invention provides a method for preparing the composite nanogranules from polymer/inorganic nanoparticle, comprising:

1) providing a first polymer;
2) forming inorganic nanoparticles in or on the first polymer or encapsulating, depositing and/or adsorbing the formed inorganic nanoparticles at the first polymer, so as to form primary composite nanogranules;
3) forming a second polymer at the primary composite nanogranule to form a secondary composite nanogranules; and 4) optionally, sequentially forming a $N^{th}$ polymer at the $(N-1)^{th}$ composite nanogranules to form a Nth composite nanogranules, where N is an integer between 3 and 20.

In a fifth aspect, the present invention provides a composition containing any of the above composite nanogranules from polymer/inorganic nanoparticle.

In a sixth aspect, the present invention provides a dispersion stabilized by the above composite nanogranules from polymer/inorganic nanoparticle, comprising a hydrophobic disperse phase and an aqueous continuous phase stabilized by the composite nanogranules from polymer/inorganic nanoparticle.

In one embodiment, the disperse phase is oil phase, and the continuous phase is aqueous phase.

In one embodiment, the disperse phase comprises active ingredient of agricultural chemicals, active ingredient of medicines, active ingredient of cosmic, ingredient of polymerizable monomers, ingredient of polymers.

In another aspect, the present invention provides an aqueous coating, comprising any of the composite nanogranules from polymer/inorganic nanoparticle.

In one embodiment of the aqueous coating according the present invention, the composite nanogranules from polymer/inorganic nanoparticle are the main film-forming material of the aqueous coating.

In one embodiment of the aqueous coating according the present invention, the composite nanogranules from polymer/inorganic nanoparticle are in the disperse phase.

In one embodiment, the aqueous coating contains other film-forming substances.

In one embodiment, the aqueous coating further contains additives used for the coatings. The additives can be any of suitable additives for aqueous coatings, for example, film-forming aids, curing agents, fillers, pigments, diluents, and/or crosslinking agents.

In one embodiment of the aqueous coating according to the present invention, wherein the aqueous coating is used as water-proof coating, woodwork coating, or anti-metal corrosion coating.

In one embodiment of the aqueous coating according to the present invention, the aqueous coating is used as water-proof coating, and the composite nanogranules from polymer/inorganic nanoparticle are secondary composite nanogranules, wherein the second polymer is formed by polymerization of a monomer composition of styrene, butyl acrylate, and methyl methacrylate by a weight ratio of 5-20:20-70:5-25.

In one embodiment of the aqueous coating according to the present invention, the aqueous coating is used as woodwork coating, and the composite nanogranules from polymer/inorganic nanoparticle are tertiary composite nanogranules, wherein the second polymer is formed by polymerization of a monomer composition of styrene, butyl acrylate, methyl methacrylate, and diacetone acrylamide by a weight ratio of 20-40:20-40:20-40:1-5, and the third polymer is formed by polymerization of a monomer composition of styrene, butyl acrylate, methyl methacrylate, and diacetone acrylamide by a weight ratio of 20-40:20-40:30-70:1-5.

In one embodiment of the aqueous coating according to the present invention, the aqueous coating is used as anti-metal corrosion coating, and the composite nanogranules from polymer/inorganic nanoparticle are tertiary composite nanogranules, wherein the second polymer is formed by polymerization of a monomer composition of styrene, butyl acrylate, methyl methacrylate, and diacetone acrylamide by a weight ratio of 30-50:30-50:10-40:1-10, and the third polymer is formed by a monomer composition of styrene, butyl acrylate, methyl methacrylate, and diacetone acrylamide by a weight ratio of 30-90:30-90:10-40:1-10.

In another aspect, the present invention further provides the use of any of the above composite nanogranules from polymer/inorganic nanoparticle for dispersing hydrophobic liquid and/or solid in a hydrophilic phase.

In another aspect, the present invention further provides the use of any of the above composite nanogranules from polymer/inorganic nanoparticle for stabilizing hydrophobic liquid and/or solid disperse phase in a hydrophilic phase.

In another aspect, the present invention further provides the use of any of the above composite nanogranules from polymer/inorganic nanoparticle as a template for dispersion polymerization in a hydrophilic phase.

In another aspect, the present invention further provides the use of any of the above composite nanogranules from polymer/inorganic nanoparticle as an emulsifier for emulsion polymerization in a hydrophilic phase.

In another aspect, the present invention further provides a method for dispersing a hydrophobic aqueous liquid and/or solid in an aqueous medium, comprising:

1) providing an aqueous medium;
2) providing one or more hydrophobic liquids and/or solids; and
3) homogenizing the one or more hydrophobic liquids and/or solids and any of the above composite nanogranules from polymer/inorganic nanoparticle in the aqueous medium.

DETAILED DESCRIPTION

1. First Polymer

In the composite nanogranules from polymer/inorganic nanoparticle according to the present invention, the first polymer can be any of appropriate, at least partially crosslinked and/or branched polymers. Generally, the first polymer is provided in the form of dry powder or dispersion suspended in a liquid medium. The liquid medium can be aqueous medium or organic solvents, such as alcohols, ketones, ethers, halogenated hydrocarbons, or the mixtures thereof. In one example, the first polymer can be nanogranules, having an average particle size of 1-500 nm, such as 1-20 nm, 20-50 nm, 50-100 nm, 100-200 nm, 200-500 nm and the like. When the first polymer is suspended in an aqueous medium, the average particle size may be different from that in dry form, for example, may become larger due to swelling. In some cases, the first polymer nanogranules can be spherical.

The first polymer can be obtained by polymerizing one or more low-molecule-weight compounds containing one or more hydrophilic groups in a solvent by radiation polymerization, such as light polymerization, where the hydrophilic groups include hydroxyl and/or carboxyl and/or amino and/or sulfonic groups, etc., and the low-molecule-weight compounds comprise lactic acid, itaconic acid, malic acid, maleic acid, amino acids, etc. The light polymerization can be performed under the light conditions provided by a xenon chloride excimer laser, a xenon lamp, a mercury lamp and the like. In the light polymerization, an photosensitive free radical polymerization initiator, such as benzophenone, etc., can be used.

Other compounds containing hydrophilic groups, for example, $C_{2-27}$ fatty acids, $C_{2-27}$ fatty alcohols, sugar alcohols, saccharides and/or amino acids, can be mixed in the low-molecule-weight compounds. The $C_{2-27}$ fatty acids comprise $C_{2-18}$ binary fatty acids and hydroxyl carboxylic acid. The $C_{2-27}$ fatty alcohols comprise $C_{2-18}$ binary fatty alcohols. The saccharides comprise sucrose, lactose, trehalose, chitosan, mannose, glucose, galactose, maltose, etc. The amino acids comprise glycine, lysine, leucine, arginine, cystine, cysteine, histidine, tryptophan, isoleucine, alanine, phenylalanine, serine, threonine, methionine, valine, tyrosine, aspartic acid and so on.

The nanogranules of the first polymer according to the present invention can be prepared by any of appropriate methods, for example, the method described in CN1530397A, which is incorporated herein by reference in its entity. The nanogranules of the first polymer according to the present invention can also be obtained by other methods than the polymers and methods described in CN1530397A.

2. Inorganic Nanoparticles

In the above composite nanogranules from polymer/inorganic nanoparticle according to the present invention, the inorganic nanoparticles can by any of suitable inorganic nanoparticles prepared in an aqueous medium, for example, silicon oxide, titanium dioxide, aluminum oxide, zinc oxide, iron oxide, cadmium selenide, zirconium oxide, etc. The inorganic nanoparticles can also be doped with other elements, such as iron, aluminum, silicon, lithium, sodium, potassium, beryllium, magnesium, calcium, strontium, barium, boron, gallium, indium, germanium, selenium, lead, nitrogen, phosphorus, arsenium, cobalt, nickel, copper, zinc, vanadium, titanium, manganese or the combinations thereof. The inorganic nanoparticles can have an average particle size of a 1-100 nm, for example, 1-5 nm, 5-10 nm, 10-20 nm, 20-50 nm, 50-100 nm and so on.

The inorganic nanoparticles can be formed in situ in an aqueous medium by using the first polymer as a template, or can be formed as a sol and then deposited on, encapsulated in, or adsorbed onto the first polymer, so as to form primary composite nanogranules. If the inorganic nanoparticles contain the above doping elements, the primary composite nanogranules can be used as the composite nanogranules from polymer/inorganic nanoparticle provided in the first aspect of the present invention.

3. Composite Nanogranules from Polymer/Inorganic Nanoparticle

In the composite nanogranules from polymer/inorganic nanoparticle, the inorganic nanoparticles can be at least partially or wholly encapsulated by the first polymer. In some cases, the inorganic nanoparticles can also be attached onto the surface of the first polymer. Each of nanogranules of the first polymer can contain one or more inorganic nanoparticles. In some cases, the nanogranules of the first polymer can contain 1 to 10, 10 to 50, 50~100, 100~1000 or more inorganic nanoparticles.

In some cases, the composite nanogranules from polymer/inorganic nanoparticle can be of spherical shape, "raspberry" shape, "rosaries" shape and/or "grape cluster" shape, etc.

A particular embodiment of the composite nanogranules from polymer/inorganic nanoparticle and the method for preparing the same provided in the first aspect of the present invention is given below, where the composite nanogranules from polymer/inorganic nanoparticle comprise polymeric nanogranules of the first polymer obtained from lactic acid by radiation polymerization, and nano-silicon oxide (or doped nano-silicon oxide) particles as the inorganic nanoparticles formed in situ on the first polymer. The preparing method comprises the steps of:

1) providing a first polymer dispersed in $C_{1-10}$ lower alcohol solution (e.g. aqueous solution), where the lower alcohol can be methanol, ethanol, propanol, isopropanol, butanol, tert-alcohol, etc.;

2) agitating and mixing aqueous silicate solution (silica aqueous dispersion) and the first polymer in a reactor, resulting in a uniformly dispersed mixture, in which, by weight percentage, the contents of silicate (or sol), the first polymer, water and alcohol are 5% to 50%, 0.3% to 30%, 50% to 90% and 1% to 10%, respectively;

3) optionally, adding doping element donator aqueous solution and acid or alkali solution for adjusting the pH value to the mixture solution obtained in step 2), where the doping element donator is at least one of titanate, $TiCl_4$, aluminum salt (halogenated aluminum, aluminum phosphate, aluminum sulfate, etc.), zinc salt ($ZnCl_2$, $ZnSO_4$, etc.), and iron salts ($FeCl_3$, $FeSO_4$, $FeCl_2$, etc.);

4) heating the mixture solution obtained in step 2) or 3) under agitation to 50-110° C. and reacting for 0.5-5 hours, so as to obtain a dispersion of the composite nanogranules from polymer/inorganic nanoparticle; and 5) optionally, removing the solvent from the mixture solution after reaction, so as to provide dried powder of the composite nanogranules from polymer/inorganic nanoparticle.

The above obtained composite nanogranules from polymer/inorganic nanoparticle, especially that obtained from silicon oxide doped with other elements, can greatly improve the dispersion and stability of oil substances, thereby be effectively applicable in the fields of water solubility and solubilization of oil substances.

As stated above, if the inorganic nanoparticles contain the above doping elements, the primary composite nanoparticles can be directly used as the composite nanogranules from polymer/inorganic nanoparticle provided in the first aspect of the invention.

However, no matter whether the inorganic nanoparticles contain the above doping elements or not, a second polymer can be formed in the primary composite nanogranules so as to from secondary composite nanogranules. The secondary composite nanogranules can be used as the composite nanogranules from polymer/inorganic nanoparticle provided in the second aspect of the invention.

Similarly, a third polymer can be formed in the secondary nanogranules so as to form tertiary composite nanogranules. The tertiary composite nanogranules can also be used as the composite nanogranules from polymer/inorganic nanoparticle provided in the second aspect of the invention.

Sequentially, a $N^{th}$ polymer can be formed in $(N-1)^{th}$ composite nanogranules so as to form $N^{th}$ composite nanogranules, where N can be selected as necessary, without particular limitation. For example, N can be an integer between 3-20, including 3, 4, 5, 6, 7, 8, 9, 10, 11, 12, 13, 14, 15, 16, 17, 18, 19 or 20. The $N^{th}$ composite nanogranules can also be used as the composite nanogranules from polymer/inorganic nanoparticle provided in the second aspect of the invention.

The second polymer to the $N^{th}$ polymer can be identical or different to one another, and usually can be selected according to desired properties of the composite nanogranules from polymer/inorganic nanoparticle. For example, the second polymer to the $N^{th}$ polymer can be formed by polymerization from one or more of the following monomers: α-olefin, vinyl chloride, acrylonitrile, vinylidene fluoride, tetrafluoroethylene, chlorotrifluoroethylene, $C_{1-20}$ alkyl esters of (meth)

acrylic acid (e.g., methyl (meth)acrylate, ethyl acrylate, butyl acrylate, octyl acrylate, octadecyl acrylate, and the like), ethylene, propylene, isobutylene, butadiene, isoprene, isocyanate compounds, styrene, vinyl benzoate, isooctyl ester, 2-chloro-2-fluorinated ethylene, methyl cinnamate, maleate, 2,4-dichloro styrene, dimethyl propylene ether, methacrylic acid, maleic anhydride, vinyl alkyl ether, vinylidene chloride, methyl chlorinated acrylate, 4-N,N-dimethylamino-2-chloro styrene, 4-chloro styrene, methyl glycol, methacrylamide dimethylamine, vinyl stearate, 2-methyl pentyl ethylene, methyl acrylamide m-toluidine, trifluoro methyl ethylene, isopropenyl methyl ketone, 3-fluoro-4-trifluoro methyl ethylene, dimethyl allyl amine, benzylidene methylene-thienyl ethyl ketone, isopropyl methyl ketone, vinyl acetate, dicyclopentadiene, benzylidene-phenethyl ketone, furfuryl acetone, vinyl octoate, hydroxyethyl methacrylate, and combinations thereof.

The second polymer to the $N^{th}$ polymer can be formed under any suitable conditions. For example, at least part of the monomer can be mixed with the initiator and optional solvent at a temperature lower than the initiation temperature, then mixed with the primary nanogranules, and then heated to above the initiation temperature so as to form the second polymer in the primary granules, thereby obtaining the secondary nanogranules; or the primary nanogranules can be mixed with water, initiator, and optional solvent, and then heated to above the initiation temperature while dripping the monomer and optional solvent to form the second polymer in the primary granules, thereby obtaining the secondary composite nanogranules.

The third polymer to the Nth polymer can be formed from the same or different monomers selected from the above monomers by similar method, thereby obtaining the tertiary composite nanogranules to the $N^{th}$ composite nanogranules.

In one particular embodiment, the primary composite nanogranules, water, initiator and optional solvent are incorporated into a reactor equipped with a reflux device, and agitated under heating. The reaction temperature is controlled between 80° C. and 95° C. The monomer is dripped into the mixture, followed by keeping the temperature for a certain period of time, filtering, and discharging to provide the final product. The secondary composite nanogranules thus obtained has a particle size of 1-1000 nm, for example 1-10 nm, 10-100 nm, 100-500 nm, 500-1000 nm, and a solid content of up to 70%. It is stable in terms of storage, dilution in water, and ion strength.

The above secondary composite nanogranules can be further formed into the third to the $N^{th}$ polymers by similar method, which can have a particle size of 1-10000 nm, for example, 1-10 nm, 10-100 nm, 100-500 nm, 500-1000 nm, 1000-10000 nm, etc.

The examples of the monomers forming the above second polymer to the Nth polymer can be selected from the combinations of the following monomers, in which the percentage is weight percentage based on the combined weight of the monomers. The initiator used for initiating the polymerization of the monomers can be aqueous initiator or oily initiator, such as ammonium persulfate, potassium persulfate, diacyl peroxide, tert-alkyl hydrogen peroxide, ditert-alkyl hydrogen peroxide, dicarbonate peroxide, azobisisobutyronitrile, benzoyl peroxide, etc.

| Monomers Combination 1 | |
|---|---|
| Styrene | 15~20% |
| butyl acrylate | 70~80% |
| iso-octyl ester | 5~7% |
| vinyl benzoate | 1~2% |
| 2,4-dichloro styrene | 1~2% |
| maleic anhydride | 0.5~1% |

| Monomers Combination 2 | |
|---|---|
| Styrene | 15~20% |
| butyl acrylate | 60~70% |
| n-octyl ester | 15~20% |
| 2-chloro-2-fluoro ethylene | 1~2% |
| vinyl alkyl ether | 1~2% |
| chloro-styrene methyl ester | 1~2% |

| Monomers Combination 3 | |
|---|---|
| butyl acrylate | 60~70% |
| methyl methacrylate | 30~35% |
| styrene | 1~2% |
| methacrylic acid | 0.5~1% |
| 2-chloro styrene | 0.5~1% |
| 4-chloro styrene | 0.5~1% |
| methacrylamide dimethylamine | 0.1~0.5% |

| Monomers combination 4 | |
|---|---|
| styrene | 30~35% |
| butyl acrylate | 30~35% |
| methyl methacrylate | 30~35% |
| acrylic acid | 0.5~1% |
| vinyl acetate | 0.5~1% |
| hydroxyethyl methacrylate | 0.5~1% |
| 3-fluoro-4-trifluoro methyl ethylene | 0.2~0.5% |

| Monomers combination 5 | |
|---|---|
| styrene | 30~35% |
| butyl acrylate | 30~35% |
| methyl methacrylate | 30~35% |
| dimethyl propenylamine | 0.5~1% |
| ethylene stearate | 1~5% |
| 4-N,N-dimethyl amino ethylene | 0.5~1% |
| methyl ethylene glycol | 0.5~1% |

| Monomers combination 6 | |
|---|---|
| styrene | 40~45% |
| butyl acrylate | 40~45% |
| methyl methacrylate | 10~15% |
| maleate | 0.5~1% |
| methyl cinnamate | 0.5~1% |
| divinyl sulfide | 0.5~1% |
| Isopropenyl methyl ketone | 0.5~1% |

| Monomers combination 7 | |
|---|---|
| styrene | 35~40% |
| butyl acrylate | 45~50% |
| methyl methacrylate | 10~25% |
| bicyclopentadiene | 0.5~1% |
| ethylene octoate | 1~2% |
| vinylidene chloride | 1~5% |
| methacrylamide-meso-toluidine | 0.5~1% |

| Monomers combination 8 | |
|---|---|
| styrene | 10~15% |
| butyl acrylate | 40~45% |
| methyl methacrylate | 40~45% |
| trifluoro-methyl ethylene | 0.5~1% |
| benzylidene-acetophenone | 0.5~1% |

| Monomers combination 9 | |
|---|---|
| styrene | 10~15% |
| butyl acrylate | 50~60% |
| methyl methacrylate | 30~35% |
| vinyl acetate | 0.5~1% |
| hydroxyethyl methacrylate | 0.5~1% |
| vinyl alkyl ether | 0.1~0.5% |

| Monomers combination 10 | |
|---|---|
| styrene | 5~10% |
| butyl acrylate | 60~65% |
| n-octoate | 25~30% |
| 2-methyl amyl vinyl | 0.1~0.5% |
| furfuryl acetone | 0.2~0.5% |
| benzylidene-thiophene ethyl ketone | 0.1~0.5% |

-continued

| Monomers combination 11 | |
|---|---|
| styrene | 35~40% |
| butyl acrylate | 35~40% |
| methyl methacrylate | 20~25% |
| maleate | 0.1~1% |
| dimethyl propylene ether | 0.5~1% |
| methyl ethylene glycol | 0.1~0.5% |
| isopropyl methyl ketone | 0.1~0.3% |

4. The Stability of the Aqueous Dispersion of Composite Nanogranules from Polymer/Inorganic Nanoparticle Due to the unique structure of the composite nanogranules from polymer/inorganic nanoparticle, it has excellent stability in the dispersion in aqueous medium. The results for the stability test performed for the above composite nanogranules from polymer/inorganic nanoparticle are as follows:
1. thermal stability: no abnormalities upon boiling at 102° C. for half an hour
2. cold stability: no abnormalities upon freezing at −20° C. and then thawing
3. base stability: no abnormalities upon adding a strong base to the emulsion
4. ion stability: no abnormalities upon adding high concentration of salts
5. solvent stability: no demulsification upon mixing the emulsion with ethanol in any ratio
6. acid stability: no abnormalities upon adding 2% acetic acid 5. The Particle Size Distribution of the Composite Nanogranules from Polymer/Inorganic Nanoparticle The composite nanogranules from polymer/inorganic nanoparticle according to the present invention generally have narrow particle size distribution. According to the statistics on some of the SEM images of the composite nanogranules from polymer/inorganic nanoparticle, it was found that the particle size of the particles generally having a particle size distribution larger than 90% is distributed within the mean of the particle size±10%. Therefore, the above composite nanogranules from polymer/inorganic nanoparticle can be considered as a mono-disperse particle system, and thus can be widely used in the cases where the particle system having narrow particle size distribution is needed.

6. The Chemical Surface Modification of the Composite Nanogranules from Polymer/Inorganic Nanoparticle The surface of the composite nanogranules from polymer/inorganic nanoparticle according to the present invention can have various groups such as carboxyl group, hydroxyl group, and/or amino group, and thus can be readily by chemical reaction grafted with various desired functional groups, for example, photosensitive crosslinking group usable in coatings, pharmaceutically active groups usable in biological medicine, etc.

7. Dispersing/Stabilizing Water Insoluble or Slightly Soluble Substances by Composite Nanogranules from Polymer/Inorganic Nanoparticle The composite nanogranules from polymer/inorganic nanoparticle according to the present invention can effectively disperse oil substances that are insoluble or slightly soluble in alcohols or water into water and alcohols to form steady dispersion. The water insoluble or slightly soluble oil substances can be active ingredients of agricultural chemicals, active ingredients of medicines, active ingredients of cosmic, polymerizable monomers, etc., which include, for example, triazophos, diazinon, chlorpyrifos, cypermethrin, acetochlor, fipronil serving as pesticide/herbicide in agricultural chemicals; taxol, astragaloside A, oridonin extracted from plants and serving as biologically active ingredients, etc.

The properties of the composite nanogranules from polymer/inorganic nanoparticle according to the present invention in improving the dispersibility and stability of the oil substances can be characterized by the parameter of oil-loading rate for olive oil.

The method for measuring oil-loading rate is described as follows: dispersing the composite nanogranules of unit mass (m) in 10 ml aqueous solution, adding various amount of olive oil (o) thereto, uniformly homogenizing at high speed, and standing for 24 hours. 1 ml dispersion is added to 50 ml deionized water, and observation is made by naked eyes. If there is no oil drops floating on the surface of the solution, it indicates that the emulsion is stable. The oil-loading rate is calculated based on the highest stable oil amount (accuracy, 1 g): oil-loading rate=o/m.

For example, 10, 11, 12, 13, 14, 15, 16, 17, 18, 19, 20, 21, 22 g olive oil were added to 10 ml aqueous dispersion of the composite nanogranules from polymer/inorganic nanoparticle (containing 2 g composite granules), which was then uniformly homogenized at high speed, and stood for 24 hours. 1 ml dispersion was added to 50 ml deionized water. The observation results showed that the samples containing olive oil of 20 g or below were stable, and small amount of oil drops were observed floating on the surface of the samples containing olive oil of 21 g and 22 g. Therefore, the oil-loading rate is 20/2=10.

8. Coatings and/or Binders Containing Composite Nanogranules from Polymer/Inorganic Nanoparticle The composite nanogranules from polymer/inorganic nanoparticle according to the present invention can be added to various coatings and/or binders as an aid to improve the properties thereof, or can be served as the main film-forming substances in coatings and/or binders. Due to the excellent water dispersibility and stability, the composite nanogranules from polymer/inorganic nanoparticle according to the present invention are especially suitable for aqueous coatings and binders.

EXAMPLES

The following examples 1-7 prepared composite nanogranules from polymer/$SiO_2$ nanoparticle and composite nanogranules from polymer/doped $SiO_2$ nanoparticle, where the first polymer as used was that prepared by the method according to example 1 in CN1530397A. In particular, the preparation process of first polymer comprises: adding 20% lactic acid and 0.1% benzophenone to a solvent of ethyl acetate, irradiating with xenon chloride excimer laser (having a wavelength of 308 nm) as a light source at room temperature, and agitating for 30 min to produce a polymer, which serves as the first polymer. The first polymer was lyophilized to provide a dried powder, which was stored in dry environment.

Example 1

Composite Nanogranules from Polymer/$SiO_2$ Nanoparticle 10 g dried powder of the first polymer was dispersed in 100 ml water, in which 800 ml 30% aqueous solution of potassium silicate was added and uniformly agitated. 10% hydrochloric acid solution was dripped into the mixture solution to a pH value of 3.5, which was then heated to 100° C. and agitated for 40 min to produce composite nanogranules from polymer/

SiO$_2$ nanoparticle. 1 g of the composite nanogranules upon lyophilization can at most stabilize 2 g olive oil in 10 ml water, that is, having an oil-loading rate of 2.

Example 2

Figure 1:
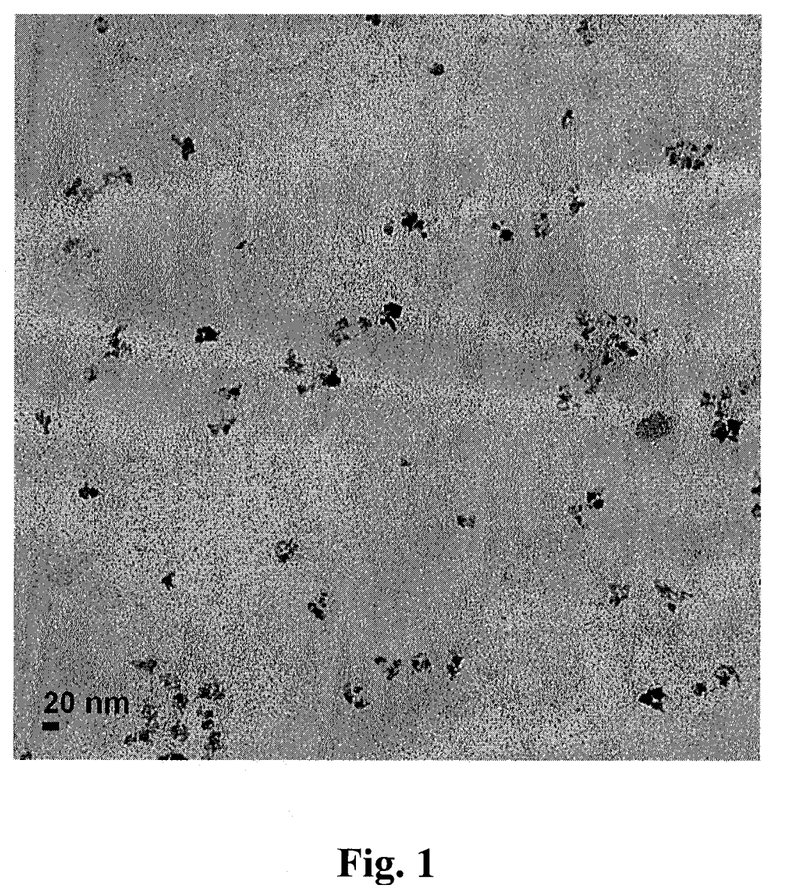
FIG. 1 is a TEM (transmission electron microscope) photograph, showing the composite nanogranules from polymer/inorganic nanoparticle according to example 2.

Composite Nanogranules from Polymer/SiO$_2$—Ti Nanoparticle 10 g dried powder of the first polymer was dispersed in 100 ml ethanol/water (in a volume ratio of 1:1), in which 800 ml 30% aqueous solution of potassium silicate was added and uniformly agitated at 50° C. for 1 hour, thereby providing stable silicate hydrosol system modified by the first polymer. 5% aqueous solution of TiCl$_4$ (50 ml) was added, and 10% hydrochloric acid solution was dripped into the mixture solution to a pH value of 3-4, which was then heated to about 100° C. and agitated for 40 min to provide the final composite nanogranules from polymer/SiO$_2$—Ti nanoparticle having a particle size of 18 nm (see FIG. 1). 1 g of the composite nanogranules upon lyophilization can stabilize up to 10 g olive oil in 10 ml water, that is, having an oil-loading rate of 10.

Example 3

Composite Nanogranules from Polymer/SiO$_2$—Zn Nanoparticle

Example 3 was performed under the same condition as in example 2, except that 50 ml 5% aqueous solution of TiCl$_4$ was changed to 50 ml 5% aqueous solution of ZnCl$_2$. Finally, composite nanogranules from polymer/SiO$_2$—Zn nanoparticle were obtained. 1 g of the composite nanogranules upon lyophilization can stabilize 5 g olive oil in 10 ml water, that is, having an oil-loading rate of 5.

Example 4

Composite Nanogranules from Polymer/SiO$_2$—Ti Nanoparticle

Example 4 was performed under the same condition as in example 2, except that 10 g of the first polymer used in example 2 was increased to 100 g. Finally, composite nanogranules from polymer/SiO$_2$—Ti nanoparticle were obtained. 1 g of the composite nanogranules upon lyophilization can stabilize 30 g olive oil in 10 ml water, that is, having an oil-loading rate of 30.

Example 5

Composite Nanogranules from Polymer/SiO$_2$—FeZn Nanoparticles

Example 5 was performed under the same condition as in example 2, except that 50 ml 5% aqueous solution of TiCl$_4$ was changed to 25 ml 4% aqueous solution of Fe$_2$(SO$_4$)$_3$ and 25 ml 1% aqueous solution of ZnCl$_2$. Finally, composite nanogranules from polymer/SiO$_2$—FeZn nanoparticle were obtained. 1 g of the composite nanogranules upon lyophilization can stabilize 6 g olive oil in 10 ml water, that is, having an oil-loading rate of 6.

Example 6

Composite Nanogranules from Polymer/SiO$_2$—TiAl Nanoparticle

Example 6 was performed under the same condition as in example 2, except that 50 ml 5% aqueous solution of TiCl$_4$ was changed to 25 ml 5% aqueous solution of TiCl$_4$ and 25 ml 1% aqueous solution of AlCl$_3$. Finally, composite nanogranules from polymer/SiO$_2$—TiAl nanoparticle were obtained. 1 g of the composite nanogranules upon lyophilization can stabilize 15 g olive oil in 10 ml water, that is, having an oil-loading rate of 15.

Example 7

Composite Nanogranules from Polymer/SiO$_2$—Ti Nanoparticle

Example 7 was performed under the same condition as in example 2, except that 800 ml 30% aqueous solution of potassium silicate used in example 2 was changed to 800 ml 30% silica sol, and 10% KOH solution was used to adjust the pH value to 3-4. Finally, composite nanogranules from polymer/SiO$_2$—Ti nanoparticle were obtained. 1 g of the composite nanogranules upon lyophilization can stabilize up to 8 g olive oil in 10 ml water, that is, having an oil-loading rate of 8.

Example 8

Secondary Composite Nanogranules 100 g primary nanogranules prepared in example 1 was dispersed in 100 g water, in which 15 g 10% ammonium persulfate, 30 g vinyl acetate, 30 g ethyl acrylate and 30 g hydroxyl butyl methacrylate were sequentially added and agitated at high speed. The obtained solution was heat to 90° C. in a water bath for reacting for 1 hours, thereby providing the final product of secondary composite nanogranules having a solid content of 20%.

Example 9

Secondary Composite Nanogranules 20 g primary nanogranules prepared in example 3 was dispersed in 100 g water, in which 1 g benzoyl peroxide, 5 g methacrylic acid, 30 g vinyl acetate, 20 g methyl methacrylate, and 10 g isooctyl acrylate were sequentially added and agitated at high speed. The obtained solution was heat to 90° C. in a water bath for reacting for 1 hours, thereby providing the final product of secondary composite nanogranules having a solid content of 30%.

Example 10

Secondary Composite Nanogranules 20 g primary nanogranules prepared in example 2 was dispersed in 100 g water, in which 13 g 10% ammonium persulfate was added. The obtained solution was poured into a 500 mL four-hole boiling flask and agitated in a water bath at 90° C., while the mixture of the following monomers was added: 40 g butyl acrylate, 40 g methyl methacrylate and 10 g methacrylic acid. The reaction was performed at 90° C. for 1 hour, providing the final product of secondary composite nanogranules having a solid content of 40%, and a particle size of 20 nm.

Example 11

Secondary Composite Nanogranules 12 g primary nanogranules prepared in example 2 was dispersed in 100 g water, in which 13 g 10% ammonium persulfate (the initiator) was added. The obtained solution was poured into a 500 mL four-hole boiling flask and agitated in a water bath at 90° C., while the mixture of the following monomers was started to be dripped into the solution when the temperature of the solution was raised above 86° C.: 50 g styrene, 120 g butyl acrylate, 120 g methyl methacrylate, and 10 g hydroxyethyl methacrylate. The dripping was performed for about 2 hours at a temperature of about 90° C., followed by maintaining the temperature of the solution for 1 hour, providing the final product of secondary composite nanogranules having a solid content of 55%.

Example 12

Secondary Composite Nanogranules 12 g primary nanogranules prepared in example 5 was dispersed in 100 g water, in which 13 g 10% potassium persulfate was added. The obtained solution was poured into a 500 mL four-hole boiling flask and agitated in a water bath at 90° C., while the mixture of the following monomers was started to be dripped into the solution when the temperature of the solution was raised above 86° C.: 50 g styrene, 120 g butyl acrylate, 120 g methyl methacrylate, and 10 g hydroxyethyl methacrylate. The dripping was performed for about 2 hours at a temperature of about 90° C., followed by maintaining the temperature of the solution for 1 hour, providing the final product of secondary composite nanogranules having a solid content of 69%.

Example 13

Figure 2:
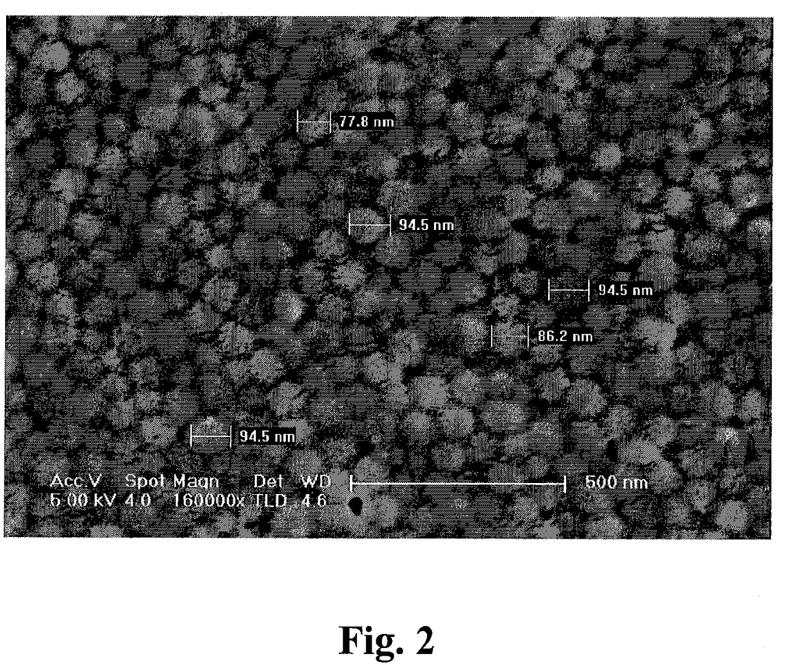
FIG. 2 is a TEM (transmission electron microscope) photograph, showing the composite nanogranules from polymer/inorganic nanoparticle according to example 13.
Figure 3:
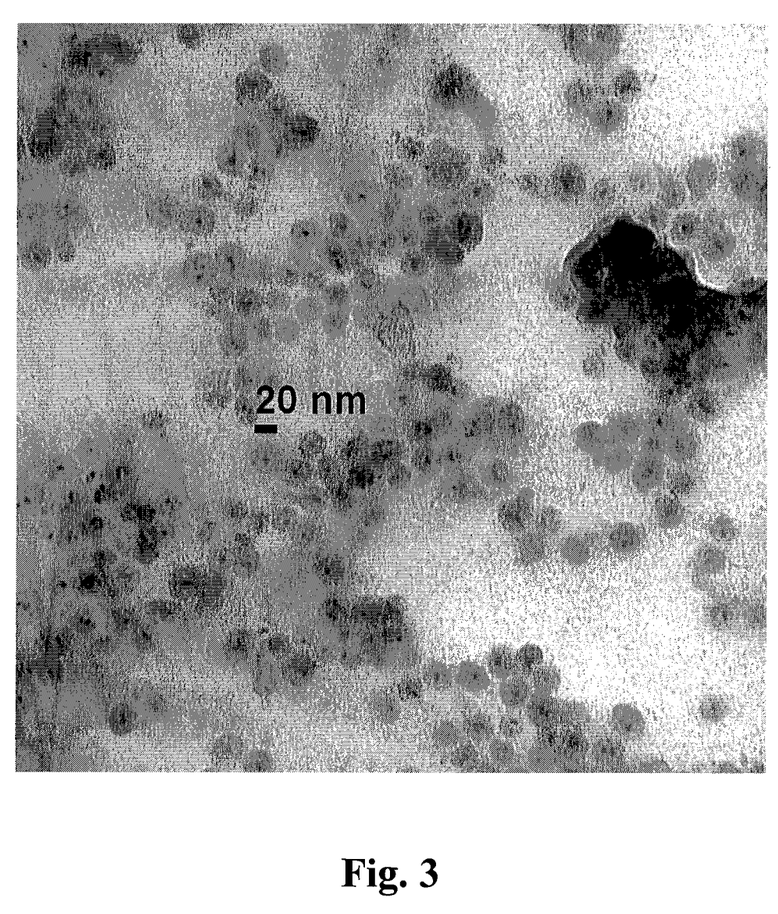
FIG. 3 is a TEM (transmission electron microscope) photograph, showing the composite nanogranules from polymer/inorganic nanoparticle according to example 17.

Tertiary Composite Nanogranules 20 g primary nanogranules prepared in example 5 was dispersed in 200 g water, in which 12 g 10% ammonium persulfate was added. The obtained solution was poured into a 500 mL four-hole boiling flask and agitated in a water bath at 90° C., while the mixture of the following monomers was started to be dripped into the solution when the temperature of the solution was raised above 86° C.: 50 g styrene, 80 g butyl acrylate, and 20 g methyl methacrylate. The dripping was completed in 1 hour, followed by agitating for 20 min, reheating to 90° C. in a water bath, and dripping the mixture of the following monomers in the mixture solution: 50 g styrene, 20 g butyl acrylate, and 20 g methyl methacrylate. The dripping was completed in about 40 min, followed by maintaining the temperature for 2 hours, and cooling, thereby providing the final product of tertiary composite nanogranules having a solid content of 50%, and a mean particle size of 92 nm (see FIG. 2).

Example 14

Quartic Composite Nanogranules 20 g primary nanogranules prepared in example 2 was dispersed in 100 g water, in which 8 g 10% ammonium persulfate was added. The obtained solution was poured into a 500 mL four-hole boiling flask and agitated in a water bath at 90° C., while the mixture of the following monomers was started to be dripped into the solution when the temperature of the solution was raised above 86° C.: 5 g cis-butadiene, 20 g methyl methacrylate, 50 g butyl acrylate, and 20 g vinyl acetate. The dripping was completed in 1 hour, followed by further agitating for 20 min, supplementing 100 g water and 5 g 10% ammonium persulfate, reheating to 90° C. in a water bath, and dripping the mixture of the following monomers in the mixture solution: 5 g divinylbenzene, 20 g styrene, 50 g butyl methacrylate, 20 g methyl methacrylate. The dripping was completed in 1 hour, followed by maintaining the temperature for 20 min under agitation, supplementing 100 g water and 5 g 10% ammonium persulfate, reheating to 90° C. in a water bath, and adding the mixture of the following monomers dropwise into the mixture solution: 50 g styrene, 20 g methyl methacrylate, and 20 g ethyl acrylate. The dropwise addition was completed in 1 hour, followed by maintaining the temperature for 1 hour, and cooling, thereby providing the final product of quartic composite nanogranules having a solid content of 60%, and a mean particle size of 5 µm.

Example 15

A coating product was obtained from the following formulation by using the secondary composite nanogranules from polymer/inorganic nanoparticle obtained in Example 11 of the present invention as the main film-forming substance.

Formulation: 100 g composite nanogranules, 60 g titanium dioxide powder, 20 g silicon micro-powder, 10 g mica power, 30 g ethanol, and suitable amount of pigments.

This coating product can be applied for the waterproof coating treatment for river banks and dams, with the substrate of cement. Due to the need for rapid coating on dams or banks in a short time period of ebbing, the coating should be dried in the short time period, and have extremely high waterproofness that can survive immersing and flushing of up to 20 hours during tide rising. Upon testing, the coating product had the following technical specifications:

(1) Easy application.

(2) Rapid drying. Under 70% humidity, it has a surface drying time of lower than 40 min at 5° C.~15° C.; a surface drying time of lower than 25 min at 15° C.~30° C.; and a surface drying time of lower than 20 min above 30° C.

(3) Extremely high waterproofness. The coating has extremely high waterproofness immediately after surface drying. It can survive for 2 min of flushing by 100 kg high-pressure water jet, and 30 days of immersing and flushing by water, without defects such as decoloring, cracking, bubbling, peeling off, eroding, etc. It has strong adherence to cement, and can not be erased off even polished by No. 04# sand paper. The coating will not be effected when being boiled for 15 min in water.

Example 16

Application in Woodwork Paints

Aqueous woodwork paints product was obtained from the following formulation by using the tertiary composite nanogranules from polymer/inorganic nanoparticle obtained in Example 13 of the present invention as the main film-forming substance.

Formulation: 100 g composite nanogranules, 1 g wetting agent, 4 g DEE film forming aid, 3 g 39235S wax, 0.5 g 51AD anti-scratching agent, small amount of defoamer, and 0.1 g 410 flatting agent.

The aqueous woodwork paint has the advantages of strong adherence, strong pigment wetting property, high powder loading rate, high color fullness, high gloss, yellow-stain resistance, etc.

Example 17

Medicine Dispersion 0.3 g secondary composite nanogranules prepared in example 10 was dispersed in 1 ml water, in which 40 mg powder of astragaloside A (plant extract), and 1 ml soybean oil were added, and uniformly agitated. Pure water was added to the obtained solution until a total volume of 10 ml, and the solution was dispersed in a high pressure homogenizer for 30 min to provide a dispersion of astragaloside A (see FIG. 3).

The obtained dispersion of astragaloside A was intragastrically administrated to mice, blood concentration of astragaloside A was measured through blood taking at different timings after administration, and the bioavailability of the medicine by oral administration was finally calculated. Surprisingly, the bioavailability of the dispersion preparation was nine times that of the powder suspension of the same medicine.

Example 18

Aqueous Acrylic Resin Coatings Having Waterproofness

The preparation of the emulsion of the film-forming matrix: 120 kg primary nanogranules prepared in example 2 and 5.3 kg ammonium persulfate were added to 800 kg water, and then the solution was heated to 85° C., in which 900 kg mixture of monomers was added dropwise under agitation. 10 min later, the aqueous solutions of 40 kg primary composite nanogranules and 15 kg acrylic acid were added dropwise over 2 hours at the same time, followed by maintaining the temperature for 1 hour to provide a second composite nanogranules serving as the emulsion of the film-forming matrix. The mixture of monomers has the following composition:

| | |
|---|---|
| styrene | 15% |
| butyl acrylate | 67% |
| methyl methacrylate | 17% |
| diacetone acrylamide | 1% |

The obtained emulsion of the film forming matrix was mixed with other ingredients of the following formulation, and agitated for 1 hour to provide the waterproof coating:

| | |
|---|---|
| emulsion of the film forming matrix | 100 weight part |
| ammonia | suitable amount to PH≈8.5 |
| DEE (film forming aid from Rhodia corporation) | 1.5 weight part |
| R996 rutile titanium dioxide powder | 35 weight part |
| precipitated barium sulfate (1250 mesh) | 12 weight part |
| silicon micro-powder (1500 mesh) | 10 weight part |

According to Chinese National Standard GB/T 9755-2001, no abnormalities were observed for the film formed by the obtained waterproof coatings after being subjected to waterproof test for 1392 hours (the standard waterproofness of high-class waterproof coatings is no abnormalities after being tested for 92 hours, according to such Standard), and no abnormalities were observed for the film after being subjected to weathering test for 2435 hours (the standard weather resistance of high-class waterproof coatings is no bubbling, peeling, cracking, chalking, or decoloring after being subjected to the weathering test for 600 hour, according to the Standard). In comparison with conventional aqueous acryl resin emulsion coatings, the present waterproof coating entails no large amount of surfactant, thereby avoiding surface defects caused by the loss of surfactant in high-humidity or water-permeating environments, and having excellent waterproofness and weather resistance.

Example 19

Aqueous Acrylic Resin Woodwork Coatings

Preparation of the emulsion of film-forming matrix: 27 kg primary composite nanogranules prepared in example 2 and 1 kg ammonium persulfate were added in 140 kg water, which was heated to 86° C. and dripped with 90 kg mixture (1) of monomers within 60 min under agitation. Then, 130 kg mixture (2) of monomers was added dropwise into the solution within 90 min under agitating, followed by cooling to 50° C., adding 16 g 10% adipic dihydrazide, further cooling, and filtering to provide tertiary composite nanogranules serving as the emulsion of film forming matrix.

The mixture (1) of monomers has the composition of:

| | |
|---|---|
| styrene | 30% |
| butyl acrylate | 33% |
| methyl methacrylate | 32% |
| diacetone acrylamide | 5% |

The mixture (2) of monomers has the composition of:

| | |
|---|---|
| styrene | 26% |
| butyl acrylate | 23% |
| methyl methacrylate | 47% |
| diacetone acrylamide | 4% |

According to the testing standard of HG/T3828-2006 for indoor aqueous woodwork coating (B class), the obtained coating had a surface drying time of lower than 30 min, a hard drying time of lower than 6 hours, a gloss of up to 87, a hardness of F, dry heat resistance against 70 degree or more, and an anti-adhesion temperature of above 75 degree.

In contrast, the presently available aqueous woodwork coating resin in the market, such as acrylic resin, polyurethane-modified acrylic resin, polyurethane, etc, are not ideal in terms of mechanical strength, hardness, and anti-adhesion of the coating. Furthermore, they are not good at gloss, waterproofness, and corrosion resistance of the coating due to the presence of surfactants.

Example 20

Aqueous Acrylic Resin Metal Coating Having Excellent Anti-Rusting Effect

Preparation of the emulsion of film forming matrix: 7 kg primary composite nanogranules prepared in example 3, 5 kg 2,2,4-trimethyl-1,3-pentanediol mono-isobutyrate, and 1.2 ammonium persulfate were added to 140 kg water, which was heated to 85° C., and dripped with 170 kg mixture (1) of monomers within 60 min under agitation. Then, 200 kg mixture (2) of monomers was dripped in the solution within 90 min under agitation, followed by maintaining at 90° C. for 1 hour, and cooling to provide tertiary composite nanogranules serving as the emulsion of film-forming matrix.

The mixture (1) monomers has the composition of:

| | |
|---|---|
| styrene | 40% |
| butyl acrylate | 38% |
| methyl methacrylate | 19% |
| diacetone acrylamide | 3% |

The mixture (2) monomers has the composition of:

| | |
|---|---|
| styrene | 35% |
| butyl acrylate | 42% |
| methyl methacrylate | 18% |
| diacetone acrylamide | 5% |

Properties evaluation:
1. coating the surface of steel plates with the above emulsion primer for 6 times at 10 min interval for each time;
2. mixing the emulsion and titanium dioxide powder by the ratio of 4:1, coating on the emulsion primer for 3 layers at 12 h interval for each layer, and maintaining for 7 days;
3. results of the anti-corrosion dipping experiments:
   1) soaking the steel plate in strong alkali solution (5% NaOH solution) for 7 days, without blistering or rusting being observed;
   2) soaking the steel plate in strong acid solution (5% sulfuric acid) for 7 days, without blistering or rusting being observed;
   3) soaking the steel plate in high salt solution (3% NaCl) for 7 days, without blistering or rusting being observed;
   4) soaking the steel plate in organic solvent (petroleum/toluene:8/2) for 48 hours, the coating being intact without blistering or rusting being observed.

The conventional aqueous anti-rusting coating materials comprise aqueous epoxide resin, aqueous acrylic resin, aqueous polyaniline resin, etc., of which the acrylic polymers have been the focus in researching anti-rusting coating base resin due to the excellent properties in high density, flexibility, anti-corrosion, anti-UV irradiation. However, for the purpose of improving anti-corrosion, large amount of zinc powder is added during use, so as to guarantee the conductivity and shielding property between the coating and steel substrates, serving for cathodic protection. Therefore, there are unneglectable environmental pollution from metal zinc and heavy metals contained therein. In contrast, the above emulsion of the acrylic resin can achieve excellent anti-rusting effect without adding any metal substance, while achieving extremely high waterproof effect by isolating air. Further, the coating film formed by the emulsion has excellent properties of high adherence to metal substrates, waterproofness, and resistance to acid, alkali, organic solvents, corrosion, UV irradiation.

The present invention is described by way of illustration. However, it should be understood that the present invention is not limited to these embodiments. Various modifications or changes can be made by those skilled in the art, without departing from the spirit and scope of the present invention.

The invention claimed is:

1. A dispersion comprising a hydrophobic disperse phase and an aqueous continuous phase stabilized by composite nanogranules, wherein the composite nanogranules comprise an inorganic nanoparticle and a first polymer, wherein the inorganic nanoparticle is encapsulated in or attached onto the first polymer, wherein the inorganic nanoparticle is silicon oxide, wherein the inorganic nanoparticle comprises a doping element selected from the group consisting of iron, aluminum, silicon, lithium, sodium, potassium, beryllium, magnesium, calcium, strontium, barium, boron, gallium, indium, germanium, selenium, lead, nitrogen, phosphorus, arsenic, cobalt, nickel, copper, zinc, vanadium, titanium, manganese, and combinations thereof, and wherein the first polymer is a copolymer of (a) at least partially branched or crosslinked polylactic acid or lactic acid with (b) a $C_{2-27}$ fatty acid, a $C_{2-27}$ fatty alcohol, a saccharide, an amino acid, or a combination thereof.

2. The dispersion according to claim 1, wherein the hydrophobic disperse phase comprises an ingredient selected from the group consisting of agricultural chemicals, medicines, cosmetics, polymerizable monomers, polymers, and combinations thereof.

3. The dispersion according to claim 2, wherein the agricultural chemicals are selected from the group consisting of triazophos, diazinon, chiorpyrifos, cypermethrin, acetochlor, and fipronil.

4. The dispersion according to claim 2, wherein the medicines are selected from the group consisting of taxol, astragaloside A and rebescensine A.

5. The dispersion according to claim 1, wherein the composite nanogranules have an average particle size of 14000 nm.

6. The dispersion according to claim 1, wherein the first polymer contains one or more hydrophilic groups selected from carboxyl group, hydroxyl group, sulfonic group and amino group.

7. The dispersion according to claim 1, wherein the saccharide is selected from the group consisting of sucrose, lactose, trehalose, chitosan, mannose, glucose, galactose, maltose; and wherein the amino acid is selected from the group consisting of glycine, lysine, leucine, arginine, cystine, cysteine, histidine, tryptophan, isoleucine, alanine, phenylalanine, serine, threonine, methionine, valine, tyrosine, aspartic acid, and a combination thereof.

8. The dispersion according to claim 1, wherein the doping element is selected from the group consisting of iron, aluminum, titanium, and a combination thereof.

* * * * *